US012589086B2

(12) United States Patent
Birman et al.

(10) Patent No.: US 12,589,086 B2
(45) Date of Patent: ***Mar. 31, 2026

(54) COMPOSITIONS AND METHODS FOR THE TREATMENT OF PRIMARY BILIARY CHOLANGITIS

(71) Applicant: Genfit, Loos (FR)

(72) Inventors: Pascal Birman, Paris (FR); Alice Roudot, Lomme (FR); David Magrez, Lambersart (FR); Benoit Noel, Gondecourt (FR)

(73) Assignee: Genfit, Loos (FR)

( * ) Notice: Subject to any disclaimer, the term of this patent is extended or adjusted under 35 U.S.C. 154(b) by 398 days.

This patent is subject to a terminal disclaimer.

(21) Appl. No.: 18/017,591

(22) PCT Filed: Aug. 25, 2021

(86) PCT No.: PCT/EP2021/073473
§ 371 (c)(1),
(2) Date: Jan. 23, 2023

(87) PCT Pub. No.: WO2022/043367
PCT Pub. Date: Mar. 3, 2022

(65) Prior Publication Data
US 2023/0301951 A1 Sep. 28, 2023

(30) Foreign Application Priority Data
Aug. 26, 2020 (EP) ..................................... 20305953

(51) Int. Cl.
A61K 31/192 (2006.01)
A61P 1/16 (2006.01)

(52) U.S. Cl.
CPC .............. A61K 31/192 (2013.01); A61P 1/16 (2018.01)

(58) Field of Classification Search
CPC ................................ A61K 31/192; A61P 1/16
See application file for complete search history.

(56) References Cited

U.S. PATENT DOCUMENTS

| | | | |
|---|---|---|---|
| 8,772,342 B2 | 7/2014 | Darteil et al. | |
| 11,185,519 B2 * | 11/2021 | Hanf .................... | A61K 31/192 |
| 11,185,520 B2 | 11/2021 | Laruelle et al. | |
| 11,331,292 B2 * | 5/2022 | Hanf ........................ | A61P 1/16 |
| 11,478,440 B2 | 10/2022 | Walczak et al. | |
| 11,484,517 B2 | 11/2022 | Walczak et al. | |
| 11,590,108 B2 | 2/2023 | Descamps et al. | |
| 11,850,223 B2 | 12/2023 | Hanf | |
| 11,857,523 B2 | 1/2024 | Hanf | |
| 11,974,997 B2 | 5/2024 | Delhomel et al. | |
| 12,053,445 B2 | 8/2024 | Hanf | |
| 12,233,038 B2 | 2/2025 | Hanf | |
| 12,290,498 B2 | 5/2025 | Hanf | |
| 12,295,927 B2 | 5/2025 | Hanf | |
| 12,295,928 B2 * | 5/2025 | Hanf .................... | A61K 31/575 |
| 12,303,480 B2 | 5/2025 | Hanf | |
| 12,310,935 B2 | 5/2025 | Hanf | |
| 2007/0197606 A1 | 8/2007 | Burczynski et al. | |
| 2015/0051145 A1 | 2/2015 | Darteil et al. | |
| 2015/0290154 A1 | 10/2015 | Roberts et al. | |
| 2022/0133666 A1 | 5/2022 | Hanf | |
| 2022/0133716 A1 | 5/2022 | Delhomel et al. | |
| 2023/0052189 A1 | 2/2023 | Petit et al. | |
| 2023/0165821 A1 | 6/2023 | (Gnft-004-301) | |
| 2023/0330048 A1 | 10/2023 | Hanf | |
| 2023/0338312 A1 | 10/2023 | Hanf | |
| 2024/0074998 A1 | 3/2024 | Hanf | |
| 2024/0074999 A1 | 3/2024 | Hanf | |
| 2024/0082185 A1 | 3/2024 | Hanf | |
| 2024/0082186 A1 | 3/2024 | Hanf | |
| 2024/0091180 A1 | 3/2024 | Hanf | |
| 2024/0156763 A1 | 5/2024 | Hanf | |
| 2024/0216312 A1 | 7/2024 | Legry et al. | |
| 2024/0216313 A1 | 7/2024 | Legry et al. | |

FOREIGN PATENT DOCUMENTS

| | | |
|---|---|---|
| CN | 101461819 A | 6/2009 |
| EP | 2982667 A1 | 2/2016 |
| JP | 2019-510046 A | 4/2019 |
| WO | WO-2005/000196 A2 | 1/2005 |
| WO | WO-2007/147880 A1 | 12/2007 |
| WO | WO-2008/087366 A2 | 7/2008 |
| WO | WO-2008/087367 A2 | 7/2008 |
| WO | WO-2012/115987 A2 | 8/2012 |
| WO | WO-2014/062938 A1 | 4/2014 |
| WO | WO-2016/127019 A2 | 8/2016 |
| WO | WO-2016/154258 A1 | 9/2016 |
| WO | WO-2017/010399 A1 | 1/2017 |

(Continued)

OTHER PUBLICATIONS

Aguilar et al., "Update on Emerging Treatment Options for Primary Biliary Cholangitis", Hepatic Medicine: Evidence and Research, 12: 69-77, (2020).
Genfit: Positive Phase 2 Results from Study of Elafibranor in Primary Biliary Cholangitis, BioSpace, (2025).
Non-Final Office Action issued in U.S. Appl. No. 17/792,217 dated Apr. 25, 2025.
Non-Final Office Action for U.S. Appl. No. 17/920,260 dated Jun. 3, 2025.
Study to Evaluate the Efficacy and Safety of Elafibranor in Patients with Primary Biliary Cholangitis (PBC) and Inadequate Response to Ursodeoxycholic Acid, ClinicalTrials.gov, (2019).
Anonymous, "GFT505 Broadens Its Therapeutic Potential," URL:http://hugin.info/143426/R/1672617/544056.pdf XP055866259 [retrieved on Nov. 26, 2021], Jan. 24, 2013.

(Continued)

*Primary Examiner* — Kevin E Weddington
(74) *Attorney, Agent, or Firm* — Morse, Barnes-Brown & Pendleton, P.C.; Martin Z. Zhang, Esq.; Russell L. Widom

(57) ABSTRACT

The invention relates to a pharmaceutical composition comprising elafibranor or a pharmaceutically acceptable salt thereof, for use to treat primary biliary cholangitis (PBC) in a subject intolerant to ursodeoxycholic acid (UDCA).

9 Claims, 3 Drawing Sheets

(56)         References Cited

FOREIGN PATENT DOCUMENTS

Figure 2:
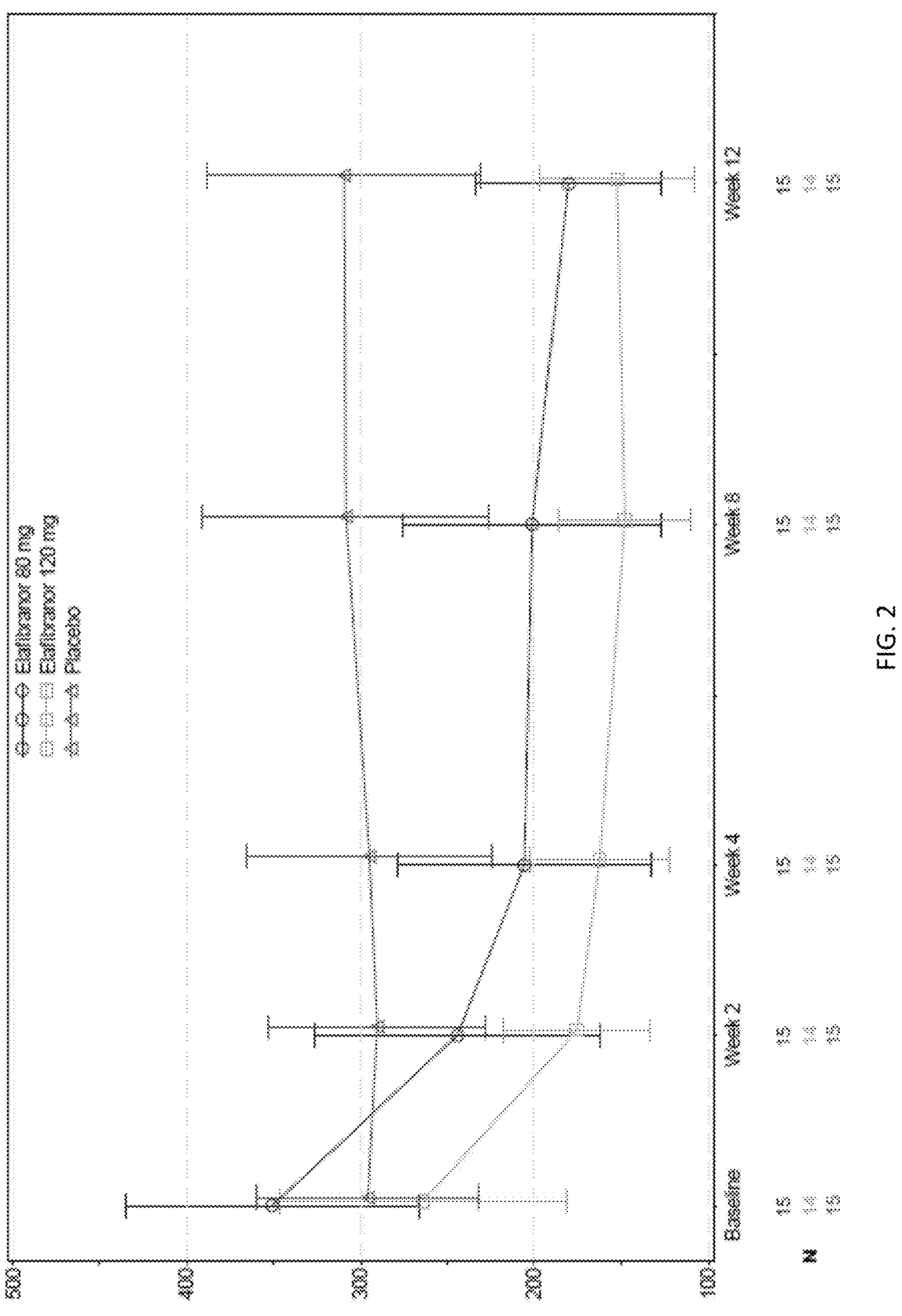

| WO | WO-2017/167935 A1 | 10/2017 |
| WO | WO-2018/060372 A1 | 4/2018 |
| WO | WO-2018/193006 A1 | 10/2018 |
| WO | WO-2019/053582 A1 | 3/2019 |
| WO | WO-2019/067373 A1 | 4/2019 |
| WO | WO-2021/059023 A1 | 4/2021 |

OTHER PUBLICATIONS

Anonymous, "Press Release Genfit Provides Pipeline Update and Launch of New Clinical," URL:https://ml-eu.globenewswire.com/Resource/Download/f248612c-5b0d-41a3-ba8d-f95a8c910e59 XP055866591 [retrieved on Nov. 26, 2021], May 11, 2021.

Araujo, et al., "PPAR gamma activation protects the brain against microvascular dysfunction in sepsis," Microvascular Research, vol. 84, No. 2, p. 218-221, Sep. 1, 2012.

Benedetta, et al., "The challenges of primary biliary cholangitis: What is new and what needs to be done," Journal of Autoimmunity, 105, 2019.

Bloomfield, et al., "Routine Ertapenem Prophylaxis for Transrectal Ultrasound Guided Prostate Biopsy does Not Select for Carbapenem Resistant Organisms: A Prospective Cohort Study", Journal of Urology, vol. 198, No. 2, p. 362-368, Mar. 10, 2017.

Bougarne, et al., "Molecular Actions of PPAR[alpha] in Lipid Metabolism and Inflammation," US vol. 39, No. 5, p. 760-802, Endocrine Reviews, Retrieved from the Internet: URL:https://academic.oup.com/edrv/article-pdf/39/5/760/25900093/er.2018-00064.pdf, Oct. 1, 2018.

Boyer-Diaz, et al., "Pan-PPAR agonist lanifibranor improves portal hypertension and hepatic fibrosis in experimental advanced chronic liver disease," Journal of Hepatology, 4(5):1188-1199, 2021.

Brink, et al., "Pharmacokinetics of once-daily dosing of ertapenem in critically ill patients with severe sepsis, International Journal of Antimicrobial Agents," vol. 33, No. 5, p. 432-436, 2009.

Busch, et al., "Delayed activation of PPAR-[beta]/[delta] improves long-term survival in mouse sepsis: effects on organ inflammation and coagulation," Innate Immunity, p. 262-273, Retrieved from the Internet: URL:https://journals.sagepub.com/doi/pdf/10.1177/1753425918771748, May 1, 2018.

Cariou, et al., "Effects of the New Dual PPARa/d Agonist GFT505 on Lipid and Glucose Homeostasis in Abdominally Obese Patients with Combined Dyslipidemia or Impaired Glucose Metabolism," Diabetes Care vol. 34, pp. 2008-2014, 2011.

Cariou, et al., "GFT505 for the treatment of nonalcoholic steatohepatitis and type 2 diabetes," Expert Opinion on Investigational Drugs, 23(10):1441-8, 2014.

Dohmen, et al., "The Effectiveness of Fenofibrate in Comparison to Bezafibrate for Patients with Asymptomatic Primary Biliary Cirrhosis," Fukuoka Acta Medica vol. 104, pp. 350-361, 2013.

El-Sisi, et al., "Effects of Three Different Fibrates on Intrahepatic Cholestasis Experimentally Induced in Rats," PPAR Research vol. 2013, pp. 1-10, 2013.

Genfit, "FDA and EMA Grant GENFIT's Elafibranor Orphan Drug Designation for Primary Biliary Cholangitis (PBC)," Retrieved online on Jul. 13, 2020.

Ghonem, et al., "Fibrates and Cholestasis," Hepatology vol. 62, pp. 635-643, 2015.

Halilbasic, et al., "Nuclear Receptors as Drug Targets in Cholestatic Liver Diseases," Clinical Liver Disease vol. 17, pp. 161-189, 2013.

Hegade, et al., "A systematic approach to the management of cholestatic pruritus in primary biliary cirrhosis," Frontline Gastroenterol;7(3):158-166, Jul. 2016.

Hegade, et al., "Drug treatment of pruritus in liver diseases," Clin Med (Lond);15(4):351-7, Aug. 2015.

Hegade, et al., "Novel Bile Acid Therapeutics for the Treatment of Chronic Liver Diseases" Therapeutic Advances in Gastroenterology vol. 9, pp. 376-391, 2015.

International Search Report for International Application No. PCT/EP2017/057634, dated Apr. 27, 2017.

International Search Report for International Application No. PCT/EP2018/052163, dated Apr. 19, 2018.

International Search Report for International Application No. PCT/EP2021/052710, dated Apr. 12, 2021.

International Search Report for International Application No. PCT/EP2021/063075, dated Jul. 15, 2021.

International Search Report for International Application No. PCT/EP2021/073473, dated Nov. 3, 2021.

International Search Report for International Application No. PCT/EP2022/062707 mailed Sep. 21, 2022.

International Search Report for International Application No. PCT/EP2022/062710 mailed May 10, 2022.

Kita, et al., "Bezafibrate may attenuate biliary damage associated with chronic liver diseases accompanied by high serum biliary enzyme levels," Journal of Gastroenterology, 41, pp. 686-692 (2006).

Kostapanos, "Current role of fenofibrate in the prevention and management of non-alcoholic fatty liver disease," World Journal of Hepatology, vol. 5, No. 9, p. 470. Jan. 1, 2013.

Krones, et al., "Future Medical Treatment of PSC" Current Hepatology Reports vol. 18, pp. 96-106, Feb. 13, 2019.

Kumar, et al, "The PPAR a/g Agonist Saroglitazar Improves Insulin Resistance and Steatohepatitis in a Diet Induced Animal Model of Nonalcoholic Fatty Liver Disease," Scientific Reports, 10(1):9330, 2020.

Liu, et al., "Early investigational drugs targeting PPAR-a for the treatment of metabolic disease," Expert Opinion on Investigational Drugs, vol. 24(5); 2015.

Marra, et al, "Thiazolidinedione Treatment Inhibits Bile Duct Proliferation and Fibrosis in a Rat Model of Chronic Cholestasis," World Journal of Gastroenterology vol. 11, pp. 4931-4938, 2005.

Nicolopoulos, et al., "Chronic Anicteric Intrahepatic Cholestasis Associated with Ankylosing Spondylitis. Beneficial Treatment by Clofibrate," Digestion vol. 24, pp. 69-72, 1982.

Non-Final Office Action for U.S. Appl. No. 17/533,767, dated Feb. 14, 2024.

Non-Final Office Action for U.S. Appl. No. 18/505,898, dated Sep. 11, 2024.

Non-Final Office Action for U.S. Appl. No. 18/506,013, dated Sep. 11, 2024.

Non-Final Office Action for U.S. Appl. No. 18/506,021, dated Sep. 4, 2024.

Non-Final Office Action for U.S. Appl. No. 18/506,029, dated Sep. 5, 2024.

Non-Final Office Action for U.S. Appl. No. 18/506,036, dated Sep. 5, 2024.

Non-Final Office Action for U.S. Appl. No. 18/506,051, dated Sep. 5, 2024.

Non-Final Office Action for U.S. Appl. No. 18/212,008, dated Aug. 29, 2023.

Non-Final Office Action for U.S. Appl. No. 18/212,029, dated Sep. 1, 2023.

Notice of Allowance for U.S. Appl. No. 18/212,008, dated Oct. 12, 2023.

Notice of Allowance for U.S. Appl. No. 18/212,029, dated Oct. 18, 2023.

Notice of Allowance for U.S. Appl. No. 18/505,898, dated Jan. 30, 2025.

Notice of Allowance for U.S. Appl. No. 18/506,013, dated Jan. 3, 2025.

Notice of Allowance for U.S. Appl. No. 18/506,021, dated Dec. 20, 2024.

Notice of Allowance for U.S. Appl. No. 18/506,029, dated Jan. 16, 2025.

Notice of Allowance for U.S. Appl. No. 18/506,036, dated Jan. 16, 2025.

Notice of Allowance for U.S. Appl. No. 18/506,051, dated Jan. 22, 2025.

Notice of Allowance for U.S. Appl. No. 17/533,767, dated May 10, 2024.

(56)            References Cited

OTHER PUBLICATIONS

Ostadhadi, et al., "The role of PPAR-gamma receptor in pruritus," European Journal of Pharmacology, 762, pp. 322-325, 2015.

Polyzos, et al., "Current and emerging pharmacological options for the treatment of nonalcoholic steatohepatitis," Metabolism: Clinical and Experimental, 111S:154203, 2020.

Ratziu, "Novel Pharmacotherapy Options for NASH," Digestive Diseases and Sciences vol. 61, pp. 1398-1405, Mar. 22, 2016.

Staels, et al., "Hepatoprotective Effects of the Dual Peroxisome Proliferator-Activated Receptor Alpha/Delta Agonist, GFT505, in Rodent Models of Nonalcoholic Fatty Liver Disease/Nonalcoholic Steatohepatitis," Hepatology vol. 58, pp. 1941-1952, 2013.

Wettstein, et al., "The New-Generation Pan-Peroxisome Proliferator-Activated Receptor Agonist IVA337 Protects the Liver From Metabolic Disorders and Fibrosis," Hepatology Communications, 1(6):524-537, 2017.

Yamashita, et al., "Pemafibrate, a New Selective PPARa Modulator: Drug Concept and Its Clinical Applications for Dyslipidemia and Metabolic Diseases," Current Atherosclerosis Reports, 22(1):5, 2020.

Yin, et al., "Dose-dependent effects of peroxisome proliferator-activated receptors [beta]/[delta] agonist on systemic inflammation after haemorrhagic shock," Cytokine, vol. 103, p. 127-132, Mar. 1, 2018.

Baschet et al "Cost-Effectiveness Analysis of Obeticholic Acid for the Treatment of Primary Biliary Cholangitis (PBC) Patients with Inadequate Response or Intolerance to Ursodeoxycholic Acid (UDCA) in France" Value in Health vol. 20, p. A556, PSY69, Oct. 1, 2017.

Chascsa et al "Emerging Therapies for PBC" The Journal of Gastroenterology vol. 55, pp. 261-272, Jan. 22, 2020.

Galoosian et al "Clinical Updates in Primary Biliary Cholangitis: Trends, Epidemiology, Diagnostics, and New Therapeutic Approaches" Journal of Clinical and Translational Hepatology vol. 8, pp. 49-60, Jan. 29, 2020.

Khanna et al "Novel Strategies and Therapeutic Options for the Management of Primary Biliary Cholangitis" Therapeutic Advances in Gastroenterology vol. 10, pp. 791-803, Jan. 1, 2017.

Beuers et al., "New paradigms in the treatment of hepatic cholestasis: From UDCA to FXR, PXR and beyond", Journal of Hepatology, 62: S25-S37 (2015).

Boyer et al., "Treatment of Chronic Cholestasis: What We Know and What We Will Know?", Clinical Liver Disease, 8 (6): 140-144 (2016).

Cariou et al., "Dual Peroxisome Proliferator-Activated Receptor $\alpha/\delta$ Agonist GFT505 Improves Hepatic and Peripheral Insulin Sensitivity in Abdominally Obese Subjects", Diabetes Care, 36: 2923-2930 (2013).

Cheung et al., "Combined ursodeoxycholic acid (UDCA) and fenofibrate in primary biliary cholangitis patients with imcomplete UDCA response may improve outcomes", Aliment Pharmacol Ther, 43: 283-293 (2016).

CymaBay Therapeutics, Pipeline, MBX-8025, Wayback Machine, Feb. 29, 2016.

Excerpt from clinicaltrials.gov, National Library of Medicine (NCT02609048), Mar. 24, 2016.

Final Office Action issued in U.S. Appl. No. 17/920,260 dated Dec. 18, 2025.

Floreani et al., "Metabolic Syndrome Associated With Primary Biliary Cirrhosis", Journal of Clinical Gastroenerology, 49: 57-60 (2015).

Floreani et al., "Proposed therapies in primary biliary cholangitis", Expert Review of Gastroenterology & Hepatology, 10 (3): 371-382 (2016).

Fruchart, "Selective peroxisome proliferator-activated receptora modulators (SPPARMα): The next generation of peroxisome proliferator-activated receptor α-agonists", Cardiovascular Diabetology, 12: 82 (2013).

Genfit Press Release, "Genfit: FDA has officially cleared the IND to proceed with Phase II trial and evaluate elafibranor in PBC" (2016).

Grigorian et al., "Fenofibrate is effective adjunctive therapy in the treatment of primary biliary cirrhosis: A meta-analysis" Clinics and Research in Hepatology and Gastroenterology, 39: 296-306 (2015).

Honda et al., "Anticholestatic Effects of Bezafibrate in Patients with Primary Biliary Cirrhosis Treated with Ursodeoxycholic Acid", Hepatology, 57(5): 1931-1941 (2013).

Iqirvo® FDA label (2024).

Jungst et al., "Intrahepatic cholestasis in common chronic liver diseases", European Journal of Chinical Investigation, 43(10): 1069-1083 (2013).

Kowdley et al., "Efficacy and Safety of Elafibranor in Primary Biliary Cholangitis", New England Journal of Medicine, 390(9): 795-805 (2024).

Lammers et al., "Levels of Alkaline Phosphatase and Bilirubin Are Surrogate End Points of Outcomes of Patients with Primary Biliary Cirrhosis: An International Follow-up Study", Gastroenterology, 147: 1338-1349 (2014).

Nozaki et al., "PPARy ligand attenuates portal inflammation in the MRL-Ipr mouse: a new strategy to restrain cholangiopathy in primary biliary cirrhosis", Med Mol Morphal, DOI 10.1007/s00795-013-0017-0 (2013).

Pawlak et al., "Molecular mechanism of PPARα action and its impact on lipid metabolism, inflammation and fibrosis in non-alcoholic fatty liver disease", Journal of Hepatology, 62: 720-733 (2015).

Ratziu et al., "An international, phase 2 randomized controlled trial of the dual PPAR $\alpha$-$\delta$ agonist GFT505 in adult patients with NASH", Hepatology, 62(1): 262A-263A (2015).

Ratziu et al., "Elafibranor, an Agonist of the Peroxisone Proliferator—Activated Receptor—$\alpha$ and -$\delta$, Induces Resolution of Nonalcoholic Steatohepatitis Without Fibrosis Worsening", Gastroenterology, 150: 1147-1159 (2-16).

Ratziu et al., "Novel Pharmacotherapy Options for NASH", Dig Dis Sci, DOI 10.1007/s10620-016-4128-z (2016).

Sahebkar et al., "New peroxisome proliferator-activated receptor agonists: potential treatments for atherogenic dyslipidemia and non-alcoholic fatty liver disease", Expert Opin. Pharmacother., 15(4): 493-503 (2014).

Sanyal et al., "Upregulated absorption of dietary saturated fatty acides with changes of intestinal fatty acid transporters in non-alcoholic steatohepatitis", Hepatology, 62(1); 1252A (2015).

Trivedi et al., "Primary biliary cholangitis: new treatments for an old disease", Frontline Gastroenterology, 8: 29-36 (2017).

WHO Drug Information, 28(4): 485-486 and 497-498 (2014).

* cited by examiner

FIG. 1

| Serum ALP (U/L) | Statistic | Elafibranor 80 mg N = 15 | Elafibranor 120 mg N = 14 | Placebo N = 15 |
|---|---|---|---|---|
| Baseline | Mean ± SD | 350.6 ± 152.1 | 263.8 ± 142.8 | 296.2 ± 115.5 |
| | Median | 321.0 | 210.0 | 246.0 |
| Endpoint (Visit 5 or EOT value) | Mean ± SD | 180.7 ± 95.7 | 152.4 ± 76.3 | 309.7 ± 142.8 |
| | Median | 161.0 | 122.0 | 262.0 |
| Relative change from baseline to Endpoint (%) | Mean ± SD | -48.3 ± 14.8 | -40.6 ± 17.4 | 3.2 ± 14.8 |
| | Median | -50.6 | -41.4 | 1.4 |
| Primary analysis - Non-parametric randomization-based ANCOVA with baseline ALP as covariate | | | | |
| Treatment effect (vs placebo)[a] | Estimate | -52.0 | -43.9 | - |
| | 95% CI | [-62.5 ; -41.5] | [-55.7 ; -32.1] | - |
| | p-value | < 0.001 | < 0.001 | - |
| Supportive Analysis – ANCOVA with baseline ALP as a covariate | | | | |
| Treatment effect (vs placebo)[b] | Estimate | -51.4 | -43.9 | - |
| | 95% CI | [-63.3 ; -39.5] | [-55.8 ; -31.9] | - |
| | p-value | < 0.001 | < 0.001 | - |
| Interaction: Baseline*trt | p-value | 0.528 | | |

COMPOSITIONS AND METHODS FOR THE TREATMENT OF PRIMARY BILIARY CHOLANGITIS

CROSS REFERENCE

This application is the national stage of International Patent Application No. PCT/EP2021/073473, filed on Aug. 25, 2021, which claims priority to European Patent Application No. 20305953.0, filed on Aug. 26, 2020, the entire contents of which are hereby incorporated by reference in their entirety.

Primary biliary cholangitis (PBC) is a rare, chronic, progressive liver disease of autoimmune etiology, characterized by injury of the intrahepatic bile ducts that, in untreated patients, may progress to hepatic fibrosis, cirrhosis, hepatic decompensation, and death unless patients receive a liver transplant. PBC disproportionately affects women vs men (approximately 10:1) and is typically diagnosed in patients between 40 years to 60 years of age. In Europe, North America, Asia, and Australia, the incidence and prevalence rates of PBC are reported as ranging from 0.33 to 5.8 per 100,000 inhabitants and 1.91 to 40.2 per 100,000 inhabitants, respectively.

Over 60% of the newly diagnosed cases are asymptomatic. The majority of asymptomatic patients become symptomatic within 10 years. The most common symptoms of PBC are fatigue and pruritus (Crosignani A, et al., Clinical features and management of primary biliary cirrhosis. World J Gastroenterol. 2008; 14(21):3313-3327). The mechanisms underlying these symptoms are not well elucidated and neither correlates with disease stage or clinical outcomes.

PBC represents one of the leading indications for liver transplantation. Despite its rarity, PBC remains therefore an important cause of morbidity in the Western world. PBC has also been identified as an important risk factor for hepatocellular carcinoma.

PBC is characterized by cholestasis caused by autoimmune destruction of biliary ductules with progressive impairment of bile flow in the liver. This results in increased hepatocellular bile acid concentrations which are toxic to the liver. Such hepatocellular injury is associated with a local inflammatory response resulting early on in an abnormal elevation of serum alkaline phosphatase (ALP) levels. Indeed, elevations in ALP level are associated with a risk of liver transplantation or death that is 2.0 to 2.5 times higher than the risk associated with normal levels. An abnormally elevated bilirubin level, which occurs later in disease progression, is also a strong predictor of outcomes, with a risk of liver transplantation or death that was 5.1 to 10.7 times the risk associated with normal levels.

The only approved drugs to treat patients with PBC are ursodeoxycholic acid (UDCA) and more recently Ocaliva® (obeticholic acid, OCA).

UDCA (Ursodeoxycholic acid) has been shown to improve ALP and bilirubin levels, and to delay histological progression, thereby increasing liver transplant-free survival. However, up to 40% of UDCA-treated patients have a suboptimal response (Ali A H, et al., Orphan drugs in development for primary biliary cirrhosis: challenges and progress. Orphan Drugs: Research and Reviews. 2015; 5:83-97). Moreover, ALP has been shown to remain elevated in up to 70% of patients who are currently being treated or are intolerant to UDCA (Lammers W J, et al., Levels of alkaline phosphatase and bilirubin are surrogate end points of outcomes of patients with primary biliary cirrhosis: an international follow-up study. Gastroenterology. 2014; 147 (6):1338-1349).

Moreover, from 3 to 5% of patients are intolerant to UDCA.

«Intolerant to UDCA» means either:

having a contraindication to be treated by UDCA, like pregnant women; patients with complete biliary obstruction of extrahepatic origin; patients with widespread intrahepatic obstruction; patients with calcified cholesterol stones, radiopaque stones or radiolucent bile pigment stones malfunctioning gallbladder, patients with acute inflammation of the gallbladder or of the biliary tract, patients with frequent biliary colic, or patients who are hypersensitive to Ursodiol® or to any ingredient in the formulation or being unable to be compliant with the UDCA medication due to serious adverse event(s) or serious condition(s). Among the possible serious adverse events or serious conditions leading to intolerance, one can cite leucopenia; ulceratis immune suppression and consequent fever; incoercible or otherwise unexplained diarrhea; pneumonia; pharyngitis; otitis media; bronchopneumonia; bronchitis; oral moniliasis; abscess formations; dysuria or recurrent watery diarrhea; stomach burns; tubulointerstitial nephritis; leukocytoclastic vasculitis; skin rash; thrombocytopenia; recurrent wheezy chest, cough or interstitial lung disease; hepatic complications such as vanishing bile duct syndrome, pruritus, cholangitis, ascites, increasing cholestasis, portal hypertension or liver cell failure; convulsions; nausea; vomiting; sleep disturbance or diabetes.

Considering the efficacy and tolerability issues with the current treatment options available, there is an unmet need for therapeutic options for patients with PBC, allowing treatment of PBC, for patients intolerant to UDCA.

Elafibranor (2-(2,6-dimethyl-4-{3 [4-(methylsulfanyl) phenyl]-3-oxopropen-1-yl}phenoxy)-2-methylpropanoic acid) is a drug currently tested in a pivotal phase III study for the treatment of PBC. Elafibranor was also evaluated in a phase II study for the treatment of PBC. The results of phase II on PBC show that the mean relative change (%) from baseline to Endpoint in serum ALP was −48.3% for the elafibranor 80 mg treatment group, −40.6% for the elafibranor 120 mg treatment group, and 3.2% for placebo. The absolute change from baseline in serum ALP was statistically significantly different from placebo at Endpoint for both the elafibranor 80 mg treatment group (p<0.001) and the elafibranor 120 mg treatment group.

Thus, the treatment with elafibranor resulted in a consistent, statistically significant reduction in plasma ALP levels from baseline when compared to placebo. Moreover, elafibranor is safe and well-tolerated by the patients.

Thus, the invention relates to a pharmaceutical composition comprising elafibranor or a pharmaceutically acceptable salt thereof for use to treat PBC for patients intolerant to UDCA.

The invention further relates to a pharmaceutical composition comprising elafibranor or a pharmaceutically acceptable salt thereof, for use in a method for the treatment of PBC in a subject having PBC and being intolerant to UDCA.

The invention also relates to a method for the treatment of PBC without provoking and/or worsening at least one adverse event associated to PBC in a UDCA-intolerant subject in need thereof, said method comprising administering to said subject a therapeutically effective amount of elafibranor or of a pharmaceutically acceptable salt thereof.

The invention further relates to a method for the treatment of PBC in a subject being intolerant to UDCA, said method comprising administering to said subject a therapeutically effective amount of elafibranor or of a pharmaceutically acceptable salt thereof.

The invention also relates to a method for the treatment of PBC in a subject having PBC and being intolerant to UDCA treatment, said method comprising administering to said subject a therapeutically effective amount of elafibranor or of a pharmaceutically acceptable salt thereof.

Illustrative methods to synthesize elafibranor include those described in PCT applications WO2004/005233, WO2005/005369 and WO 2011/144579.

According to the present invention, the pharmaceutical composition of the invention may include a stereoisomer of elafibranor or of GFT1007, or a salt of elafibranor or of GFT1007.

In some embodiments of the invention, GFT1007, the active metabolite of elafibranor, is used. GFT1007 is 2-[2, 6-dimethyl-4-[3-[4-(methylthio)phenyl]-3-oxo-propyl]phenoxy]-2-methylpropanoic acid. Its properties and synthesis were described in PCT application WO2007/147879, where it is referred to as compound 1.

A stereoisomer is an isomeric compound that has the same molecular formula and sequence of bonded atoms, but differs in the 3D-dimensional orientations of its atoms in space. The stereoisomers include enantiomers, diastereoisomers, cis-trans and E-Z isomers, conformers and tautomers.

Elafibranor or GFT1007 can be formulated as pharmaceutically acceptable salt, particularly an acid or base salt compatible with pharmaceutical use. Salts of elafibranor or GFT1007 implemented herein include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

In particular, "pharmaceutically acceptable salts" include inorganic as well as organic acids salts. Counter-ions may be selected from the following the non-exhaustive list: ammonia, L-arginine, benethamine, benzathine, tert-butylamine (erbumine), calcium hydroxide, choline hydroxide, deanol, diethanolamine (2,2'-iminobis(ethanol), diethylamine, epolamine (1-(2-hydroxyethyl)pyrrolidine), 2-(diethylamino)-ethanol, ethanolamine (2-aminoethanol), ethylenediamine, glycine, hydrabamine, 1H-imidazole, L-Lysine, magnesium hydroxide, meglumine (N-methyl-glucamine), 4-(2-hydroxyethyl)-morpholine, piperazine, potassium hydroxide, sodium hydroxide, triethanolamine (2,2',2''-nitrilo-tris(ethanol)), tromethamine, zinc hydroxide, in particular tromethamine, potassium, sodium, benethamine, benzathine, L-arginine, ethanolamine, meglumine, glycine, erbumine, L-lysine, epolamine, choline, preferably tromethamine, potassium, sodium, benethamine, benzathine, L-arginine, more preferably tromethamine, potassium, sodium, L-arginine, more particularly tromethamine.

In particular embodiments, the invention implements an ammonia, L-arginine, benethamine, benzathine, tert-butylamine (erbumine), calcium, choline, deanol, diethanolamine (2,2'-iminobis(ethanol), diethylamine, epolamine (1-(2-hydroxyethyl)pyrrolidine), 2-(diethylamino)-ethanol, ethanolamine (2-aminoethanol), ethylenediamine, glycine, hydrabamine, 1H-imidazole, L-Lysine, magnesium, meglumine (N-methyl-glucamine), 4-(2-hydroxyethyl)-morpholine, piperazine, potassium, sodium, triethanolamine (2,2', 2''-nitrilo-tris(ethanol)), tromethamine or zinc salt of elafibranor or GFT1007. In a further particular embodiment, the salt of elafibranor or GFT1007 is selected from a tromethamine, potassium, sodium, L-arginine, benethamine, benzathine, ethanolamine, meglumine, glycine, erbumine, L-lysine, choline, epolamine, magnesium or 2-amino-2-methyl-propan-1-ol salt of elafibranor or GFT1007.

Elafibranor or GFT1007 (in particular elafibranor) or a pharmaceutical salt thereof may be formulated in a pharmaceutical composition.

Pharmaceutical compositions used in the invention can comprise one or several excipients or vehicles, acceptable within a pharmaceutical context (e.g. saline solutions, physiological solutions, isotonic solutions, etc., compatible with pharmaceutical usage and well-known by one of ordinary skill in the art). This composition can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. Elafibranor can be formulated for enteral or parenteral administration. For example, elafibranor can be formulated for oral, intravascular (e.g. intravenous or intra-arterial), intramuscular, intraperitoneal, subcutaneous, transdermal or nasal administration. The pharmaceutical composition can be a solid or liquid dosage form. Illustrative formulations include, without limitation, an injectable suspension, or suspension for oral ingestion, a gel, an oil, a pill, a tablet, a suppository, a powder, a gel cap, a capsule, an aerosol, an ointment, a cream, a patch, or means of galenic forms for a prolonged and/or slow release.

As disclosed herein, the term "treatment" or "treating" refers to an improvement, the prophylaxis of a disease or disorder, or at least one symptom can be discerned therefrom. This also means an improvement, prevention of at least one measurable physical parameter associated with the disease or disorder being treated, which is not necessarily discernible in the subject. "Treatment" or "treating" further refers to inhibiting or slowing the progression of a disease or disorder, physically, stabilization of a discernible symptom, physiologically, for example, stabilization of a physical parameter, or both. "Treatment" or "treating" also refers to delaying the onset of a disease or disorder. In some particular embodiments, compounds of interest are administered as a preventive measure. In this context, "prevention" or "preventing" refers to a reduction in the risk of acquiring a disease or disorder specified.

The terms "patient," "subject," "individual," and the like are used interchangeably herein, and refer to any human or non-human mammalian subject, including humans, laboratory, domestic, wild or farm animals. In certain non-limiting embodiments, the patient, subject or individual is a human. Preferably the subject is a human patient whatever its age or sex, where new-borns, infants, children, adults are included. Preferably, the patient is between 40 years to 60 years of age. Preferably, the patient is a woman.

As detailed above, from 3 to 5% of patients are intolerant to UDCA. «Intolerant to UDCA» or "intolerant to treatment with UDCA" means either:

having a contraindication to be treated by UDCA, like pregnant women; patients with complete biliary obstruction of extrahepatic origin; patients with widespread intrahepatic obstruction; patients with calcified cholesterol stones, radiopaque stones or radiolucent bile pigment stones malfunctioning gallbladder, patients with acute inflammation of the gallbladder or of the biliary tract, patients with frequent biliary colic, or patients who are hypersensitive to Ursodiol® or to any ingredient in the formulation or being unable to be compliant with the UDCA medication due to serious adverse event(s) or serious condition(s). Among the possible serious adverse events or serious conditions leading to intolerance, one can cite leucopenia; ulceratis immune suppression and consequent fever; incoercible or otherwise unexplained diarrhea; pneumonia; pharyngitis; otitis media; bronchopneumonia; bronchitis; oral moniliasis; abscess formations; dysuria or recurrent watery diarrhea; stomach burns; tubulointerstitial nephritis; leukocytoclastic vasculitis; skin rash; thrombocytopenia; recurrent wheezy chest, cough or interstitial lung disease; hepatic complications such as vanishing bile duct syndrome, pruritus, cholangitis, ascites, increasing cholestasis, portal hypertension or liver cell failure; convulsions; nausea; vomiting; sleep disturbance or diabetes.

As used herein, the term "therapeutically effective amount" refers to a quantity of elafibranor which prevents, removes or reduces PBC and one of its adverse events. In particular, the amount of pharmaceutical salt of elafibranor is intended as the amount of free form of elafibranor in this pharmaceutical salt.

The quantity to be administered can be adapted by a person skilled in the art. In particular, doses and regimen of administration may be function of the stage and of the severity of PBC to be treated, as well as of the weight, the age and the global health of the subject to be treated, as well as of the judgment of the doctor.

In a particular embodiment, elafibranor or a pharmaceutically acceptable salt thereof is administered at a dose varying between 10 mg and 200 mg per administration, preferentially between 80 mg and 120 mg per administration. In a further particular embodiment, elafibranor or a pharmaceutically acceptable salt thereof is administered at a dose of 80 mg per administration. In another particular embodiment, elafibranor or a pharmaceutically acceptable salt thereof is administered at a dose of 120 mg per administration.

In yet another embodiment, elafibranor, a pharmaceutically acceptable salt thereof, or a pharmaceutical composition comprising the same is administered orally. Preferably, elafibranor, a pharmaceutically acceptable salt thereof, or a pharmaceutical composition comprising the same is orally administered once a day.

According to an embodiment, the pharmaceutical composition is a solid dosage form, such as a tablet. In a further particular embodiment, said tablet comprises between 10 mg and 200 mg of elafibranor or a pharmaceutically acceptable salt thereof, such as between 80 mg and 120 mg of elafibranor or a pharmaceutically acceptable salt thereof. For example, a tablet may comprise 80 mg of elafibranor or a pharmaceutically acceptable salt thereof or 120 mg of elafibranor or a pharmaceutically acceptable salt thereof.

In yet another embodiment, a tablet comprising 80 mg of elafibranor is orally administered once a day.

DESCRIPTION OF THE FIGURES AND TABLES

Abbreviations used in the figures, in the tables, and in the text:
Ab Antibody
ABV alcohol by volume
ADR adverse drug reaction
AE adverse event

6

AESI adverse event of special interest
AFP alfa-fetoprotein
AIH autoimmune hepatitis
ALD alcoholic liver disease
ALP alkaline phosphatase
ALT alanine aminotransferase
AMA anti-mitochondrial antibodies
ANA antinuclear antibodies
ANCOVA analysis of covariance
AST aspartate aminotransferase
AT aminotransferase
AUCss area under curve steady state
BP blood pressure
BUN blood urea nitrogen
C4 serum $7\alpha$-hydroxy-4-cholesten-3-one
CA cholic acid
CCl4 carbon tetrachloride
CDCA chenodeoxycholic acid
CI confidence interval
CK-18 cytokeratin-18
CKD-EPI chronic kidney disease-epidemiology collaboration
CPK creatine phosphokinase
CRF case report form
CRO clinical research organization
CSR clinical study report
CT computed tomography
CYP cytochrome P450
DB double blind
DCA deoxycholic acid
DDI drug-drug interaction
DILI drug-induced liver injury
DSUR development safety update report
EAIR exposure adjusted incidence rates
ECG electrocardiogram
eCRF electronic case report form
eGFR estimated glomerular filtration rate
ELF enhanced liver fibrosis
ELISA enzyme-linked immunosorbent assay
EOT end-of-treatment
ePRO electronic patient-reported outcomes
FGF19 fibroblast growth factor 19
FPG Fasting plasma glucose
GCA glycocholic acid
GCDCA glycochenodeoxycholic acid
GCP good clinical practice
GDCA glycodeoxycholic acid
GGT gamma-glutamyl transferase
GLCA glycolithocholic acid
HAV hepatitis A virus
HBsAg hepatitis B surface antigen
hCG human chorionic gonadotropin
HCV hepatitis C virus
HCV Ab hepatitis C virus Antibody
HDL-C High-density lipoprotein cholesterol
hHSC human hepatic stellate cells
HIV human immunodeficiency virus
HRQoL health-related quality of life
hsCRP high sensitivity C-reactive protein
ICE Intercurrent event
ICF Informed Consent Form
IgG immunoglobulin G
IgM immunoglobulin M
IL interleukin
INR international normalized ratio
IRT interactive response technology
ITT intent-to-treat LCA lithocholic acid
LDL-C low-density lipoprotein cholesterol
LLN lower limit of normal
LTE long term extension
LVDB last visit double blind
MCP monocyte chemotactic protein
MDR3 multidrug resistance protein type 3
MDRD modification of diet in renal disease
MELD-Na model for end-stage liver disease-sodium
MMRM mixed model with repeated measurement
MRI magnetic resonance imaging
NA not applicable
NASH nonalcoholic steatohepatitis
NF-κB nuclear factor kappa B
NOAEL no observed adverse effect level
NRS numeric rating scale
OATP1B3 organic anion transporting polypeptide 1B3
OCA obeticholic acid
PAI plasminogen activator inhibitor
PBC primary biliary cholangitis
PBI placebo-based multiple imputation
PDGF platelet-derived growth factor
PGIC patient global impression of change
PGIS patient global impression of severity
PK pharmacokinetics
PKS pharmacokinetics set
PP per-protocol
PPAR peroxisome proliferator-activated receptor
PRO patient reported outcome
PSC primary sclerosing cholangitis
PT prothrombin time
QoL quality of life
RNA ribonucleic acid
SADR serious adverse drug reaction
SAE serious adverse event
SAP statistical analysis plan
SD standard deviation
SMA smooth muscle antibodies
SOP standard operating procedure
SS safety set
SUSAR suspected unexpected serious adverse reaction
SV screening visit
TB total bilirubin
TC total cholesterol
TCA taurocholic acid
TCDCA taurochenodeoxycholic acid
TDCA taurodeoxycholic acid
TE transient elastography
TG triglycerides
TGF-β transforming growth factor beta
TIPS transjugular intrahepatic portosystemic shunts
TLCA taurolithocholic acid
TNFα tumor necrosis factor-alpha
Trt treatment
UDCA ursodeoxycholic acid
ULN upper limit of normal
Urine ACR urine albumin to creatinine ratio
UV-LLNA UV-local lymph node assay
VLDL very low density lipoprotein
WBC white blood count
WOCBP women of childbearing potential
FIG. 1: Relative Change from Baseline in Serum Alkaline Phosphatase at Endpoint—Primary Efficacy Endpoint—Primary and Supportive Analyses
ALP=alkaline phosphatase; ANCOVA=analysis of covariance; CI=confidence interval; EOT=end-of-treatment; SD=standard deviation; trt=treatment.

[a]Non-parametric randomization-based ANCOVA with baseline ALP as a covariate. p-values were computed under the null hypothesis (based on re-randomizations of the population) while estimates and CIs were computed under the alternative hypothesis (based on repeated random sampling).
[b]ANCOVA with baseline ALP as covariate and without interaction term.
FIG. 2: Mean Alkaline Phosphatase Values from Baseline through Week 12 by Treatment Group
FIG. 3: Mean Relative Change from Baseline through Week 12 in Alkaline Phosphatase by Treatment Group

EXAMPLES

Example 1: Drug Used

Elafibranor (2-(2,6-dimethyl-4-{3-[4-(methylsulfanyl)phenyl]-3-oxopropen-1-yl}phenoxy)-2-methylpropanoic acid) was supplied as 80 mg white to offwhite round coated tablets with no printed inscription.
A placebo tablet (of the same size as the corresponding active tablet) to match elafibranor 80 mg was provided as a white to off-white round coated tablet with no printed inscription. The placebo tablet contained the same excipients as the active formulation as well as lactose monohydrate (which was used in place of the active ingredient).

Example 2: Results on ALP Levels

Figure 3:
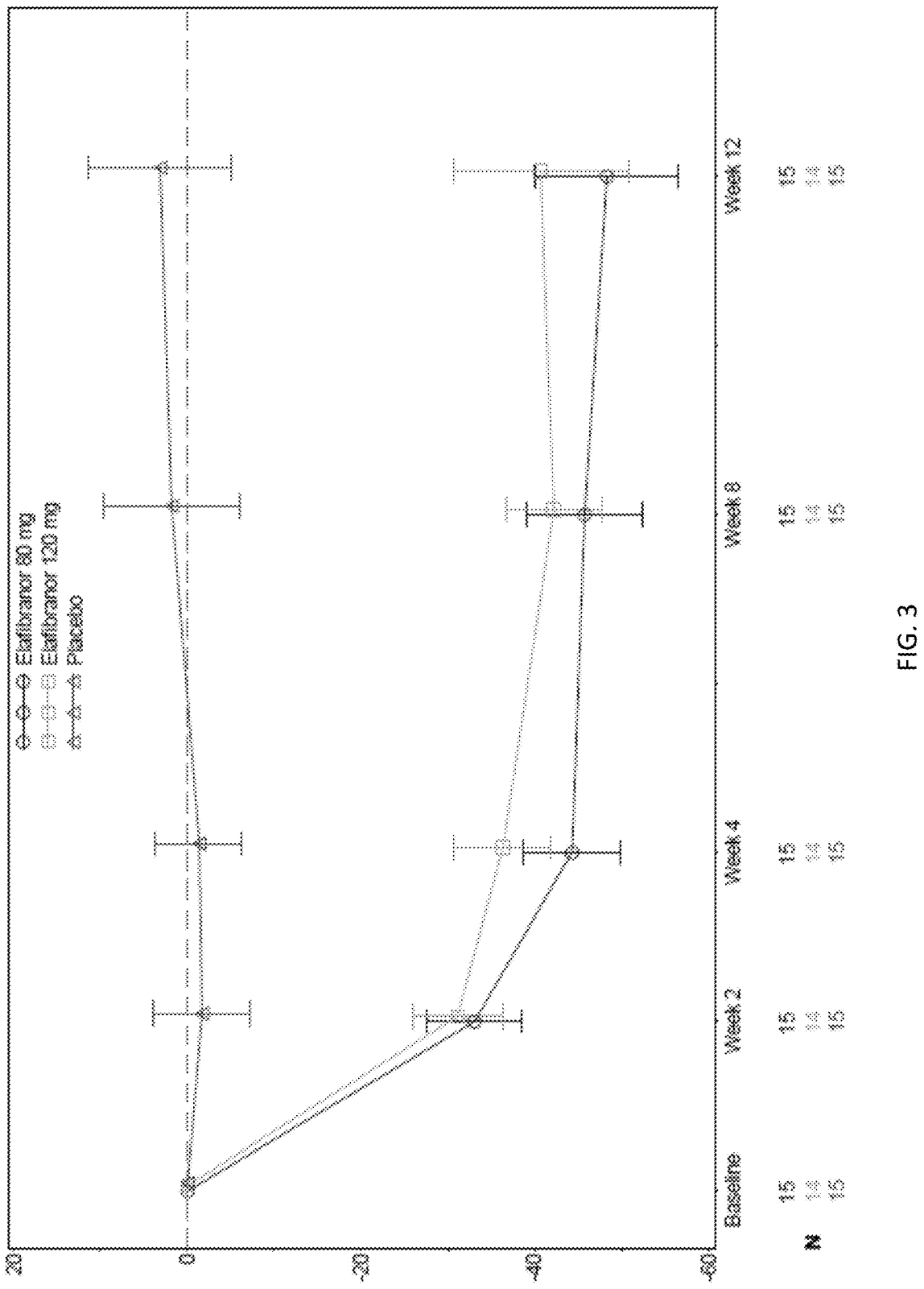

The mean relative change (%) from baseline to Endpoint in serum ALP was −48.3% for the elafibranor 80 mg treatment group, −40.6% for the elafibranor 120 mg treatment group, and 3.2% for placebo.
In the primary efficacy analysis conducted using a non-parametric randomization-based ANCOVA with baseline ALP as covariate, each dose demonstrated a statistically significant treatment effect vs placebo (p<0.001). The treatment effect estimate was −52.0% (95% CI [−62.5; −41.5]) for the elafibranor 80 mg treatment group and −43.9% (95% CI [−55.7; −32.1]) for the elafibranor 120 mg treatment group (FIG. 1).
The primary efficacy supportive analysis conducted using an ANCOVA with baseline ALP as a covariate was consistent with the primary efficacy analysis. The treatment effect estimate was −51.4% (95% CI [−63.3; −39.5]) for the elafibranor 80 mg treatment group and −43.9% (95% CI [−55.8; −31.9]) for the elafibranor 120 mg treatment group (FIG. 1).
The mean (95% CI) ALP values from baseline through Week 12 are shown in FIG. 2 by treatment group. Both the elafibranor 80 mg and 120 mg treatment groups demonstrated declining mean ALP values over the 12 week study.
The mean (95% CI) relative changes (%) in ALP values from baseline through Week 12 are shown in FIG. 3 by treatment group. The mean relative changes (%) from baseline shows a decrease in ALP values over time for the elafibranor 80 mg and 120 mg treatment groups beginning at Week 2 and continuing up through Week 12.
The relative change from baseline in serum ALP was statistically significantly different from placebo at Endpoint for both the elafibranor 80 mg treatment group and the elafibranor 120 mg treatment group.

Example 3: Clinical Trial for PBC

A double-blind (DB), randomized, placebo-controlled, phase 3 study and Open-Label long term extension clinical trial is conducted in patients with Primary Biliary Cholangitis and intolerance to ursodeoxycholic acid to evaluate the efficacy and safety of treatment with elafibranor given orally (80 mg daily).

In the DB period, patients are randomized in a 2:1 ratio to receive elafibranor 80 mg or placebo, once daily. The DB period will last until the last completed week 52 (V6) or until a maximum of 104 weeks DB period, whichever happens first, to further collect safety and clinical outcomes data in a DB manner. After the DB period, all patients receive elafibranor 80 mg daily for up to 5 years during the LTE period.

Primary Endpoint

The primary endpoint is to evaluate the effect of elafibranor (80 mg/day) on cholestasis over 52 weeks of the treatment compared to placebo in patients intolerant to ursodeoxycholic acid (UDCA).

Secondary Objectives

The secondary objectives are:

1) To evaluate the effect of elafibranor (80 mg/day) on normalisation of alkaline phosphatase (ALP) over 52 weeks of the treatment compared to placebo
2) To evaluate the effect of elafibranor (80 mg/day) on pruritus over 52 weeks of the treatment compared to placebo
3) To evaluate the effect of elafibranor (80 mg/day) over 52 weeks of treatment compared to placebo on:
   a) hepatobiliary injury and liver function markers
   b) inflammation and hepatic fibrosis
   c) lipid parameters
   d) bile acids
   e) pruritis Patient Reported Outcomes (PROs)
   f) patient-reported Fatigue
   g) patient-reported Sleep
   h) health-related Quality of Life (HRQoL)
   i) health utility
   j) liver histology (both efficacy and safety criteria)
   k) safety and tolerability
4) To determine the pharmacokinetics (PK) parameters of elafibranor and its active metabolite GFT1007, at steady state following daily oral administration at 80 mg in PBC patients presenting intolerance to UDCA treatment
5) To evaluate the effect of elafibranor (80 mg/day) during the LTE period on:
   a) safety and tolerability
   b) maintenance of efficacy from the DB period Inclusion Criteria Patients must meet all of the following inclusion criteria to be eligible for randomization into the study:

1) Must have provided written informed consent and agree to comply with the study protocol
2) Males or females age of 18 to 75 years inclusive at first Screening Visit (SV)
3) Definite or probable PBC diagnosis as demonstrated by the presence of ≥2 of the following 3 diagnostic criteria:
   a. History of elevated ALP levels for ≥6 months prior to randomization (V1)
   b. Positive anti-mitochondrial antibodies (AMA) titers (>1/40 on immunofluorescence or M2 positive by enzyme-linked immunosorbent assay [ELISA]) or positive PBC-specific antinuclear antibodies (ANA)
   c. Liver biopsy consistent with PBC 4) Patients in whom it is safe and practical to proceed with a liver biopsy, and who agree to have:
   a. 1 liver biopsy during the Screening Period (if no historical biopsy within 12 months before screening is available)
   b. 1 liver biopsy after 52-weeks of treatment
5) ALP≥1.67× upper limit of normal (ULN)
6) Total bilirubin (TB)≤2×ULN. To ensure adequate representation of moderately advanced disease or patients at risk of progression to clinical outcomes, at least 10% of randomized patients will be moderately advanced per Rotterdam Criteria (TB>ULN or Albumin<lower limit of normal [LLN]) and at least 20% will have a TB>0.6×ULN (patients at risk of progression)
7) Must have at least 4 available values for PBC Worst Itch Numeric Rating Scale (NRS) during each of the 7 day intervals in the 14 days prior to randomization (V1), for a total of at least 8 values for PBC Worst Itch NRS in the last 14 days prior to randomization (V1)
8) Unable to tolerate UDCA treatment (no UDCA for ≥3 months) prior to randomization (per country standard-of-care dosing)
9) If on colchicine must be on a stable dose for ≥3 months prior to randomization
10) Medications for management of pruritus (e.g., cholestyramine, rifampin, naltrexone or sertraline) must be on a stable dose for ≥3 months prior to randomization
11) Patients taking statins or ezetimibe must be on a stable dose for ≥2 months prior to randomization
12) Females participating in this study must be of non-child bearing potential or must be using highly efficient contraception for the full duration of the study and for 1 month after the last drug intake:
   Non-child bearing potential: cessation of menses for at least 12 months due to ovarian failure or surgical sterilization such as bilateral oophorectomy, hysterectomy, or medically documented ovarian failure for >6 months prior to randomization
   If required by local Institutional Review Board (IRB)/ Independent Ethics Committee (IEC) and/or national regulations, sexual abstinence may be considered adequate (the reliability of sexual abstinence needs to be evaluated in relation to the duration of the clinical study and the preferred and usual lifestyle of the patient)
   Using a highly effective non-hormonal medical contraception (bilateral tubal occlusion, vasectomized partner or intra-uterine device) for ≥3 months prior to screening
   Highly effective contraception with barrier or highly effective hormonal method of contraception (oral, intravaginal or transdermal combined estrogen and progestogen hormonal contraception associated with inhibition of ovulation, oral, injectable or implantable progestogen-only hormonal contraception associated with inhibition of ovulation or intrauterine hormone-releasing system). The hormonal contraception must be started at least one month prior to screening.

Exclusion Criteria:

Patients presenting any of the following exclusion criteria will not be eligible for randomization into the study:

1) History or presence of other concomitant liver disease including:
   a) positive anti-hepatitis A virus (HAV) immunoglobulin M (IgM) antibodies or positive hepatitis B surface antigen (HBsAg) or positive anti-hepatitis C virus (HCV) ribonucleic acid (RNA) (tested for in case of known cured HCV infection or positive HCV Ab at screening)

b) primary sclerosing cholangitis (PSC)

c) alcoholic liver disease (ALD)

d) autoimmune hepatitis (AIH) or if treated for an overlap of PBC with AIH, or if there is suspicion and evidence of overlap AIH features, that cannot be explained alone by insufficient response to UDCA e) nonalcoholic steatohepatitis (NASH)

f) Gilbert's Syndrome (exclusion due to interpretability of bilirubin levels)

g) known history of alpha-1 antitrypsin deficiency

2) Clinically significant hepatic decompensation, including:

a) history of liver transplantation, current placement on a liver transplant list, current Model for End-Stage Liver Disease-Sodium (MELD-Na) score≥12 linked to hepatic impairment b) patients with cirrhosis/portal hypertension complications, including known esophageal varices, ascites, history of variceal bleeds or related interventions (e.g., insertion of variceal bands or transjugular intrahepatic portosystemic shunts [TIPS]), and hepatic encephalopathy, history or presence of spontaneous bacterial peritonitis, hepatocellular carcinoma c) hepatorenal syndrome (type I or II)

3) medical conditions that may cause non-hepatic increases in ALP (e.g., Paget's disease) or which may diminish life expectancy to <2 years, including known cancers 4) Patient has a positive test for Human Immunodeficiency Virus (HIV) Type 1 or 2 at screening, or patient is known to have tested positive for HIV 5) evidence of any other unstable or untreated clinically significant immunological, endocrine, hematologic, gastrointestinal, neurological, or psychiatric disease as evaluated by the investigator 6) other clinically significant medical conditions that are not well controlled or for which medication needs are anticipated to change during the study 7) history of alcohol abuse, defined as consumption of more than 30 g pure alcohol per day for men, and more than 20 g pure alcohol per day for women, or other substance abuse within 1 year prior to screening visit (SV1)

8) for female patients: known pregnancy, or has a positive urine pregnancy test (confirmed by a positive serum pregnancy test), or lactating 9) administration of the following medications are prohibited as specified below:

a) 2 months prior to randomization and throughout the study (up to the last study visit): fibrates and glitazones b) 3 months prior to randomization and throughout the study (up to the last study visit): obeticholic acid (OCA), azathioprine, cyclosporine, methotrexate, mycophenolate, pentoxifylline, budesonide and other systemic corticosteroids; potentially hepatotoxic drugs (including α-methyl-dopa, sodium valproic acid isoniazid, or nitrofurantoin)

c) 12 months prior to randomization and throughout the study (up to the last study visit): antibodies or immunotherapy directed against interleukins (ILs) or other cytokines or chemokines 10) patients who are currently participating in, plan to participate in, or have participated in an investigational drug study or medical device study containing active substance within 30 days or five half-lives, whichever is longer, prior to screening; patients with previous exposure to seladelpar are excluded.

11) patients with previous exposure to elafibranor

12) SV value of alanine aminotransferase (ALT) and/or aspartate aminotransferase (AST)>5×ULN 13) SV value of albumin<3.0 g/dL 14) severely advanced patients according to Rotterdam criteria (TB>ULN and albumin<LLN)

15) SV value of international normalized ratio (INR)>1.3 due to altered hepatic function 16) SV value of creatine phosphokinase CPK>2×ULN 17) screening serum creatinine>1.5 mg/dL 18) significant renal disease, including nephritic syndrome, chronic kidney disease (defined as patients with markers of kidney failure damage or estimated glomerular filtration rate [eGFR]<60 mL/min/1.73 m2) calculated by modification of diet in renal disease (MDRD)

19) platelet count<150×103/μL 20) alfa-fetoprotein (AFP)>20 ng/mL with 4-phase liver computed tomography (CT) or magnetic resonance imaging (MRI) suggesting presence of liver cancer Randomization Patients who satisfy all eligibility criteria will be randomized in a 2:1 ratio to one of the following groups:

elafibra nor 80 mg placebo

A central randomization system (Interactive Voice/Web Response system (IXRS)) is used.

The randomization is stratified on two factors (ALP>3× ULN or bilirubin>ULN and Worst Itch score averaged—over the 14 days preceding baseline—≥4) at baseline (V1). During the LTE period, all patients will receive elafibranor 80 mg, once daily, for up to 5 years.

To ensure inclusion of a relevant ratio of patients with substantial risk of long term clinical outcome moderate disease stage, a minimum of 15 patients (at least 10% of the total randomized patients) present a TB above ULN or albumin below LLN and a minimum of 30 patients (at least 20% of the total randomized patients) present a TB above 0.6×ULN.

Primary Endpoint

The primary endpoint is the Response to treatment at week 52 defined as ALP<1.67×ULN and TB≤ULN and ALP decrease≥15%.

Secondary Endpoint

Response to treatment based on ALP normalization at week 52.

Change in pruritus from baseline through week 52 on PBC Worst Itch NRS score.

Other Secondary Endpoints:

1) Change from baseline in ALP at 4, 13, 26, 39 and 52 weeks

2) ALP response defined as 10%, 20% and 40% ALP reduction from baseline at week 52

3) Response to treatment at week 52 according to:

a) ALP<1.5×ULN, ALP decrease≥40% and TB≤ULN b) ALP<3×ULN, AST<2×ULN and TB≤1 mg/dL (Paris I)

c) ALP≤1.5×ULN, AST≤1.5×ULN and TB≤1 mg/dL (Paris II)

d) TB response rate of 15% change e) Normalization of abnormal TB and/or albumin (Rotterdam)

f) TB≤0.6×ULN g) ALP≤1.67×ULN and TB≤1 mg/dL h) No worsening of TB defined as level of TB≤ULN at week 52 or no increase from baseline of more than 0.1×ULN at week 52

4) PBC risk scores at week 52: United Kingdom (UK) PBC score and GLOBE score

5) Response based on bilirubin normalization (TB≤ULN) at week 52

6) Response based on albumin normalization at week 52

7) Change from baseline to week 52 in hepatobiliary injury and liver function as measured by AST, ALT, gamma-glutamyl transferase (GGT), 5' NT, total and conjugated bilirubin, albumin, INR and ALP fractionated (hepatic)

8) Change from baseline to week 52 in biomarkers of inflammation as measured by high-sensitivity CReactive Protein (hsCRP), fibrinogen, haptoglobin and tumor necrosis factor-alpha (TNF-α)

9) Change from baseline to week 52 in immune response as measured by immunoglobulin G (IgG) and IgM 10) Change from baseline to week 52 in biomarkers, non-invasive and invasive measures of hepatic fibrosis as measured by enhanced liver fibrosis (ELF)(HA, PIINP, TIMP-1), plasminogen activator inhibitor-1 (PAI-1), transforming growth factor beta (TGF-β), cytokeratin-18 (CK-18) (M65 and M30), Pro-C3 and liver stiffness measured by Transient Elastography (TE) (continuous)

11) Change from baseline to week 52 in lipid parameters as measured by total cholesterol (TC), low-density lipoprotein cholesterol (LDL-C), high-density lipoprotein cholesterol (HDL-C), calculated VLDL-C and TG 12) Change from baseline to week 52 in fasting plasma glucose (FPG)

13) Change from baseline to week 52 in bile acids and biomarkers of bile acid synthesis as measured by bile acids, serum 7α-hydroxy-4-cholesten-3-one (C4) and fibroblast growth factor 19 (FGF-19)

14) Proportion of patients with no worsening of pruritus from baseline to week 52 as measured by the PBC Worst Itch NRS 15) Response in PBC Worst Itch NRS defined as at least 30% reduction from baseline of NRS at week 52 in patients with a baseline NRS≥4

16) Change from baseline to week 52 in 5D-Itch

17) Change from baseline to week 52 in Patient Reported Outcome Measurement Information System (PROMIS) Fatigue Short Form 7a 18) Change from baseline to week 52 in the Epworth Sleepiness Scale (ESS)

19) Change from baseline to week 52 in PBC-40

20) Change from baseline to week 52 in health utility as measured by the EQ-5D-5L 21) Onset of clinical outcomes described as a composite endpoint composed of:

a) Progression to histological cirrhosis for non cirrhotic patients at baseline b) MELD-Na>14 for patients with baseline MELD-Na≤12 c) Liver transplant d) Uncontrolled ascites requiring treatment e) Hospitalization for new onset or recurrence of any of the following:

i) variceal bleed ii) hepatic encephalopathy defined as West-Haven/Conn score of 2 or more iii) spontaneous bacterial peritonitis f) Death 22) Change from baseline in the histological scores a) Fibrosis stage according to Nakanuma scoring b) Bile duct scores c) Cholangitis activity d) Interface Hepatitis activity e) Stage of disease (Sum of Fibrosis stage by Nakanuma and Bile duct score)

f) Other exploratory scores (Fibrosis according to mdodifeid Ishak scoring, portal inflammation, uctular reaction, cholestasis, concentric periductal fibrosis)

23) Safety and tolerability as assessed by a) Serious adverse events (SAEs), adverse events (AEs), adverse events of special interest (AESIs), physical examination, vital signs, medical history, electrocardiogram (ECG)

b) Chemistry and hematology c) Liver markers d) Renal biomarkers (including urinalysis)

e) Other biochemical safety markers f) Histology

24) PK assessed by elafibranor and GF1007 concentrations measurement in plasma

It is expected that elafibranor induces a significant reduction in serum ALP from baseline to end of treatment in patients presenting an intolerance to UDCA, compared to placebo. In addition, it is expected that elafibranor induces significant improvement in at least one of the secondary endpoints in these patients.

The invention claimed is:

1. A method of treating primary biliary cholangitis (PBC) comprising administering to a patient a pharmaceutical composition comprising 2-(2,6-dimethyl-4-{3-[4-(methylsulfanyl)phenyl]-3-oxopropen-1-yl}phenoxy)-2-methylpropanoic acid (elafibranor) or a pharmaceutically acceptable salt thereof, wherein the patient suffers from PBC and is intolerant to treatment with ursodeoxycholic acid (UDCA).

2. The method according to claim 1, wherein the patient has a contraindication to be treated by UDCA or is unable to be compliant with the UDCA-medication due to an adverse event or condition.

3. The method according to claim 2, wherein the patient having a contraindication to be treated by UDCA is a pregnant woman; a patient with complete biliary obstruction of extrahepatic origin; a patient with widespread intrahepatic obstruction; a patient with calcified cholesterol stones, radiopaque stones or radiolucent bile pigment stones, malfunctioning gallbladder; a patient with acute inflammation of the gallbladder or of the biliary tract; or a patient with frequent biliary colic.

4. The method according to claim 2, wherein the adverse event or condition is leucopenia; ulcerates; immune suppression and consequent fever; incoercible or otherwise unexplained diarrhea; pneumonia; pharyngitis; otitis media; bronchopneumonia; bronchitis; oral moniliasis; abscess formations; dysuria or recurrent watery diarrhea; stomach burns; tubulointerstitial nephritis; leukocytoclastic vasculitis; skin rash; thrombocytopenia; recurrent wheezy chest, cough or interstitial lung disease; hepatic complications such as vanishing bile duct syndrome, pruritus, cholangitis, ascites, increasing cholestasis, portal hypertension or liver cell failure; convulsions; nausea; vomiting; sleep disturbance; or diabetes.

5. The method according to claim 1, wherein said pharmaceutical composition is a tablet, injectable suspension, gel, oil, pill, suppository, powder, gel cap, capsule, aerosol, or a prolonged or slow release dosage form.

6. The method according to claim 1, wherein said pharmaceutical composition is for oral administration once a day.

7. The method according to claim 1, wherein elafibranor or a pharmaceutically acceptable salt thereof is administered at a dose varying between 10 mg and 200 mg per administration.

8. The method according to claim 1, wherein elafibranor or a pharmaceutically acceptable salt thereof is administered at a dose varying between 80 mg and 120 mg per administration.

9. The method according to claim 8, wherein said pharmaceutical composition is a tablet comprising 80 mg of elafibranor.

\* \* \* \* \*